United States Patent
Vallot

(10) Patent No.: US 6,186,932 B1
(45) Date of Patent: Feb. 13, 2001

(54) SACHETS FOR BIO-PHARMACEUTICAL FLUID PRODUCTS

(75) Inventor: Bernard Vallot, Marseille (FR)

(73) Assignee: Stedim, Z. I. des Paluds, Aubagne (FR)

( * ) Notice: Under 35 U.S.C. 154(b), the term of this patent shall be extended for 0 days.

(21) Appl. No.: 09/432,805

(22) Filed: Nov. 3, 1999

Related U.S. Application Data

(62) Division of application No. 09/143,236, filed on Aug. 28, 1998, now Pat. No. 5,988,422.

(30) Foreign Application Priority Data

Jul. 16, 1998 (FR) .................................................. 9809244

(51) Int. Cl.$^7$ .................................................. B31B 49/04
(52) U.S. Cl. .................. 493/189; 493/210; 493/218; 493/219; 493/243; 493/405; 493/408
(58) Field of Search .................... 493/189, 210, 493/218, 219, 231, 243, 297, 374, 379, 405, 408

(56) References Cited

U.S. PATENT DOCUMENTS

| | | | |
|---|---|---|---|
| 3,277,798 | * 10/1966 | Krauss | 93/35 |
| 3,373,915 | * 3/1968 | Anderson et al. | 229/3.5 |
| 3,413,898 | * 12/1968 | Calvert | 93/35 |
| 3,549,451 | * 12/1970 | Kugler | 156/272 |
| 3,599,539 | * 8/1971 | Coverstone | 93/35 SB |
| 3,827,341 | * 8/1974 | Stage | 93/35 R |
| 3,924,521 | * 12/1975 | Hanson et al. | 93/35 SB |
| 4,720,872 | * 1/1988 | Kaczerwaski | 383/8 |
| 5,149,315 | * 9/1992 | Muhs | 493/189 |
| 5,788,121 | 8/1998 | Sasaki et al. . | |
| 5,814,382 | * 9/1998 | Yannuzzi, Jr. | 428/34.3 |
| 5,851,072 | 12/1998 | LaFleur . | |

* cited by examiner

Primary Examiner—Peter Vo
Assistant Examiner—Sam Tawfik
(74) Attorney, Agent, or Firm—Browdy and Neimark

(57) ABSTRACT

A flexible sachet for transporting bio-pharmaceutical liquids with a volume of 50 liters or more, of the bellows type, assumes when filled a substantially parallelepiped shape. It comprises a bottom wall, a top wall and four lateral walls. It is made of a single laminated film with three or more layers, the innermost layer being a plastics material layer that can be heat welded and is biocompatible with the media transported. A method of manufacturing the sachet is also disclosed.

9 Claims, 3 Drawing Sheets

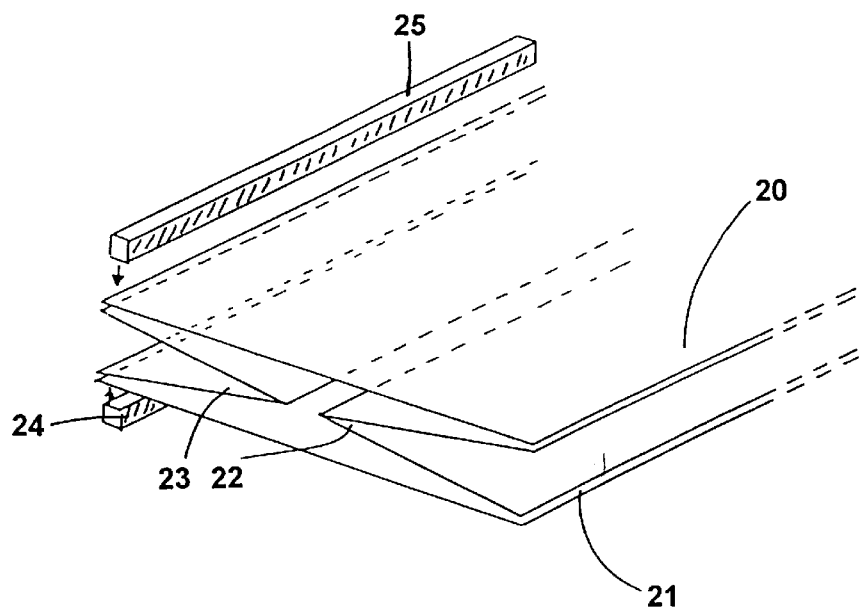
Fig. 3
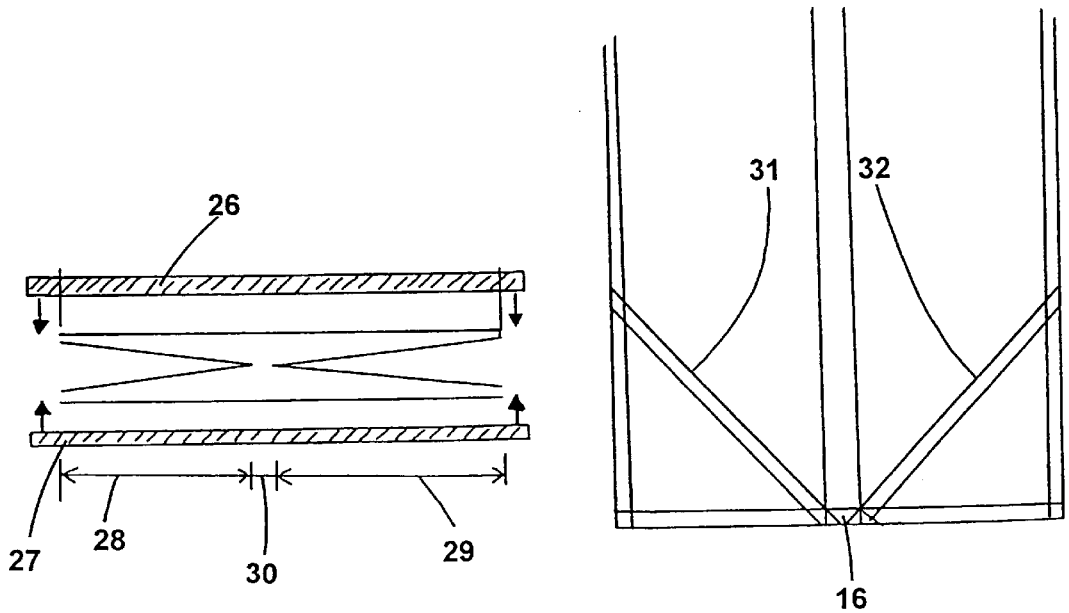
Fig. 4
Fig. 5

SACHETS FOR BIO-PHARMACEUTICAL FLUID PRODUCTS

CROSS-REFERENCE TO RELATED APPLICATIONS

This is a division of parent application Ser. No. 09/143,236, filed Aug. 28, 1998, now U.S. Pat. No. 5,988,422, the contents of which is hereby incorporated by reference.

BACKGROUND OF THE INVENTION

1. Field of the Invention

The present invention concerns new flexible sachets for transporting bio-pharmaceutical fluid products and a method of manufacturing them.

2. Description of the Prior Art

U.S. Pat. Ser. No. 350,080 describes sachets which can be used for cellular culture media and their rigid transportation container.

The bio-pharmaceuticals industry, understood in the broadest sense, is increasingly using flexible sachets with capacities in the range 20 liters to 2,000 liters and more, in particular bio-compatible sachets, to transport fluids use in the industry, such as culture media, cellular cultures, buffer solutions, artificial nutrient liquids, blood products or derived products such as plasma.

Sometimes the products contained in such sachets are used thousands of kilometers from the place where the sachets were filled. These products are often extremely valuable in financial terms and often extremely valuable in terms of the health of persons because they can be used to manufacture medication for human use, for example. It is therefore essential for such sachets to reach their destination safely, filled with the liquid with which they were initially filled, and free of contamination.

Flexible sachets of the above kind are subject to many kinds of stress during transportation: acceleration, braking, tossing, shaking, vibration, etc. and therefore to many forces including shear forces which tend to deteriorate the film from which they are made, especially at sensitive locations such as folds. Consequently these various stresses frequently lead to weakening, rupture or piercing of the sachets.

It must be remembered that sachets of the above kind intended to contain the previously mentioned liquid products and media are by their very nature provided with a number of access ports enabling their content to be filled, drawn off, mixed, etc., for example, and usually with a number of tubes installed at some or all of these access ports. The tubes are themselves often fitted with one or more rigid material devices such as valves, filters or clamps which can contribute to abrasion of the upper part of the sachets when they are transported over long distances. A hole in the top of a sachet can be just as serious as one elsewhere, for example in the situation of transporting sterile contents.

This is why it would therefore be desirable to have a sachet for transporting bio-pharmaceutical liquids with a volume of 50 liters or more which in addition to the usual qualities of such sachets, i.e. biocompatibility, sterilizability, impermeability to gases and in particular to oxygen, would be particularly resistant to transportation over long distances and easy to manufacture.

Sachets for transporting bio-pharmaceutical liquids in the form of bellows with walls constructed by manually welding three separate independent films are known in themselves.

Sachets of the above type are sold by HyClone Laboratories, for example. They have capacities in the range 1 liter to 1,000 liters, for example. However, when transported over long distances, given the many stresses to which the sachets are subjected, a number of them are lost because of leaks.

OBJECT AND SUMMARY OF THE INVENTION

This is why the subject matter of the present application is a flexible sachet for transporting bio-pharmaceutical liquids with a volume of 50 liters or more, of the bellows type, assuming when filled a substantially parallelepiped shape, comprising a bottom wall, a top wall and four lateral walls, which is made of a single laminated film with three or more layers, and preferably made of four pieces of the said single laminated film, the innermost layer being a plastics material layer that can be heat welded and is biocompatible with the media transported.

The bio-pharmaceutical liquids transported can be culture media, cell cultures, buffer solutions, artificial nutrient liquids, blood products or derivatives such as plasma, for example.

The sachet of the invention is a bellows type sachet, i.e. one in which, when laid flat, two opposite sides of the sachet are folded inwards.

The expression "laminated single film" or "monofilm" means that the film from which the walls of the sachet are made appears to be a single film although in fact it is made from a plurality of layers of films of different kinds stuck together.

In accordance with the invention, the laminated single film comprises at least three layers and preferably four layers.

The inside layer is a layer of plastics material that can be heat welded and is biocompatible with the media transported. These plastics materials include polyolefins, for example, and preferably polyethylene (PE), especially low-density and in particular ultra-low-density polyethylene.

The thickness of this layer can be in the range 50 $\mu$m to 200 $\mu$m, for example, and in particular in the range 100 $\mu$m to 200 $\mu$m.

The intermediate layer constituting a barrier to gases such as oxygen, carbon dioxide or water vapor, is for example made of polyamide (nylon) 6, polyamide 8, polyamide 11, polyamide 12, polyamide 6-6, polyamide 6-10, polyamide –6 or polyamide 6/polyamide 6-6 copolymers. Mixtures of gas barrier polymer resins can also be used such as a mixture of polyamide or polyethylene and ethylene/vinyl alcohol copolymer (EVOH) in polyvinylidene chloride (PVDC). A plastics material that has been surface treated with aluminum oxide or silica can equally be used. Under preferred conditions of implementation, the gas barrier intermediate layer is made of an ethylene/vinyl alcohol copolymer.

The thickness of this layer can be in the range 6 $\mu$m to 20 $\mu$m, for example, and in particular in the range from 10 $\mu$m to 20 $\mu$m.

The external layer is preferably made from a plastics material that has an insulating effect vis a vis heat welding, for example polyolefin or polyamide resin and preferably polyester (PET) resin.

The thickness of this layer can be in the range 10 $\mu$m to 30 $\mu$m, for example, and in particular in the range 10 $\mu$m to 20 $\mu$m.

Under preferred conditions of implementation of the invention the laminated film includes a fourth layer which is advantageously between the external layer and the gas barrier intermediate layer, improving the mechanical strength of the laminated single film.

This second intermediate layer can be of polyolefin or PET, for example, and is preferably of polyamide, advantageously polyamide 6.

The adhesive used to attach the various layers together is preferably one of the adhesives conventionally used in the field of laminated polymer films. An epoxy adhesive is preferably used, in particular one of the polyurethane-polyester type.

The above polymers can be mixed with additives. For example, the polyethylene of the inner layer can have a slippery agent added to it such as erucylamide in a concentration of 600 ppm and/or a silicon oxide at a concentration of 2,000 ppm.

Under preferred conditions of implementation of the invention, the above sachet is made from four pieces of film by flat heat welding.

This parallelepiped shape can in particular be obtained by cutting the edges of the film at 30° to 60° and approximately 45° relative to the vertical axis of the sachet.

By definition, the "bottom face" and the "top face" of the sachet are the faces of the sachet such that the welds cross over on these faces but are parallel to each other on the "lateral" faces of the sachet.

Under other preferred conditions of implementation of the invention, the above sachet has on its top face a preferably elongate flange for mounting connectors comprising one or more chimneys for fitting connectors which are preferably identical, and in particular aligned, comprising two substantially cylindrical concentric lips.

These chimneys can advantageously cooperate with connectors having a cylindrical end sized to be inserted between the lips of the chimney. Their number is preferably in the range 1 to 8, in particular 2 to 6, especially 3 to 5.

Under preferred conditions of implementation the connectors further comprise an outer skirt surrounding the outer lip of the access chimney.

The connectors can have any conventional configuration such as, for example, fittings for tubes such as, for example, fittings for small, medium or large diameter tubes, stoppers, right-angle connections, and these connectors, in particular those for right-angle connections, can themselves comprise a double-lip system similar to that of the chimneys for connectors, for example.

Under other preferred conditions of implementation of the invention the flange for mounting connectors is made of polyolefin resin and preferably of an ethylene-5 vinyl acetate copolymer.

Under other preferred conditions of implementation of the invention the connectors are glued to the chimneys using a solvent or non-solvent glue.

The present invention also consists in a sachet of the above kind fitted with connectors installed on the above chimneys.

Under other preferred conditions of implementation of the invention all the materials used to construct the sachet of the invention and its accessories are capable of withstanding exposure to radiation and other known sterilization techniques.

Under other preferred conditions of implementation of the invention the flange for mounting connectors carrying the chimneys is heat welded to the sachets.

Under other preferred conditions of implementation of the invention the mounting flange has in its lower part, opposite the access chimneys, one or in particular several spaced protuberances constituting passages, for example semi-toroidal passages, which prevent the plate being pressed totally against the bottom of the sachet when it is emptied.

Under further preferred conditions of implementation of the invention the mounting flange has standardized chimneys enabling easy customization of the outlet accessories and valves (stopper, angled or straight outlet, variety of diameters, etc.)

Under other preferred conditions of implementation of the invention the bottom face of the sachet is fitted with a bung, for example an evacuation or filling bung. The evacuation or filling bung can be mounted on the sachet in the same way as the above plate. Under preferred conditions of implementation of the invention the bung includes a 90° outlet.

Under further preferred conditions of use of the invention the emptying bung is mounted on a base installed in such a manner that it projects outwardly of the bottom of the sachet. The projecting part of the bung is preferably of polygonal shape or of any other non-circular shape, such as elongate oval, triangular, square, hexagonal, etc. This particular shape allows good centering of the sachet when the latter is installed in a rigid container for transportation by cooperation with an orifice of complementary shape and corresponding located on the bottom of the container. Also, the corners of the sachet can fit closely into the corners of the container without risk of twisting of the sachet. The bung can at the same time constitute a point at which the sachet is anchored to the bottom of the container, which improves transport.

Under other preferred conditions of implementation, the pro-eminent base of the bung has a peripheral groove which can cooperate with a clip so that it can be clipped when it is fitted into the container for filling. In this way the original position of the sachet is preserved.

The present invention also consists in a method of manufacturing a sachet as defined hereinabove from a single laminated film wherein a top film, a bottom film and two lateral films folded on themselves with their innermost panel facing to the exterior are paid out and stacked in such a manner as to bring the heat weldable plastics material layers into contact with each other and in a flat configuration, with the two lateral films located between the top and bottom film with a gap between the two lateral films, followed by heat welding of the sides two by two and of the top and bottom of the sachet.

Under preferred conditions of implementation of the invention the top and bottom welds of the sachet are K-welds, the branches of the K being inclined at approximately 45° to the direction of movement of the pieces of multilayer monofilm, for example in the range 30° to 60°, as in the examples hereinafter.

Under preferred conditions of implementation of the invention the heat welding is effected using heating bars. A single weld can be effected at a given location. However, one, two or in particular three successive welds are preferably effected. In the case of welds in a plurality of steps, the steps are preferably effected at different temperatures.

Under other preferred conditions of implementation of the invention the welds are effected with a width in the range 5 mm to 20 mm, preferably 5 mm to 15 mm and in particular 8 mm to 15 mm.

The other operations, such as cutting the films at the welds, are conventional.

It is therefore possible to proceed in a single step to a plurality of welding operations at the same level, given the presence of the external layer which has an insulating effect vis a vis heat welding. Thus only the internal layer are welded together.

BRIEF DESCRIPTION OF THE DRAWINGS

The invention will be described in more detail with reference to the accompanying drawings, in which:

FIG. 3 represents a perspective view of the placement of four films and two longitudinal heating bars (for welding one side of a sachet) during the manufacture of a sachet.

FIG. 4 represents a front view of the films and of two transverse heating bars (for welding the top and the bottom of a sachet) during the manufacture of a sachet.

FIG. 5 represents a top view of the location of the top or bottom welds of a sachet.

DETAILED DESCRIPTION OF THE PREFERRED EMBODIMENTS

EXAMPLE 1

Fabrication of a Four-layer Film

A laminated film with the following structure is made by gluing:

| Resin | Thickness |
| --- | --- |
| PET | 12 µm |
| Polyurethane-polyester epoxy adhesive | 2.5 µm |
| PA6 | 15 µm |
| Polyurethane-polyester epoxy adhesive | 2.5 µm |
| EVOH | 12 µm |
| Polyurethane-polyester epoxy adhesive | 2.5 µm |
| Ultra-low density PE | 150 µm |

EXAMPLE 2

Fabrication of a Sachet

On an automatic machine designed for this purpose, four spools of plastics material film from example 1 are paid out to constitute the four walls of a cubic or parallelepiped-shape sachet: two films are stretched flat (top and bottom) and two films are conformed as flat bellows and inserted between the first two.

The four longitudinal welds are executed by effecting three 30 cm to 90 cm longitudinal weld sections in succession in accordance with a predetermined advance movement of the film. Each of the three welds is effected at a different temperature.

This method guarantees the strength of the welds, and minimum overlap between the welded film sections and the welding bars so that the height of the sachet can be varied.

The sachet top and bottom welds are effected one after the other by the same method and with a minimum of one weld and preferably with three successive welds at different temperatures.

The sachet top and bottom welds are effected by a set of welding bars situated:

on the one hand, at 90° to the advance movement of the film, enabling welding of a section comprising 4+2+4 thicknesses of film ("transverse" weld,) and on the other hand, at an angle in the range 30° to 60° relative to the advance movement of the film in order for the sachet deployed in three dimensions to conform exactly to the geometry of the bottom and the sides of a rigid container in which it will be placed ("K" weld).

The above transverse and K welds are effected at the exact intersection of the two films of the bellows with the two flat films. This ensures that the sachet is sealed and strong.

Between the operations of effecting the top and bottom sachet welds (transverse and K welds) the following three complementary operations are effected to impart to the sachet the required features for filling and emptying from the top and from the bottom:

1) die-cutting the flat top and/or bottom film, 2) installing a flange for connectors and/or a bung, 3) heat welding the flat film(s) to the connector and/or bung(s).

Figure 1:
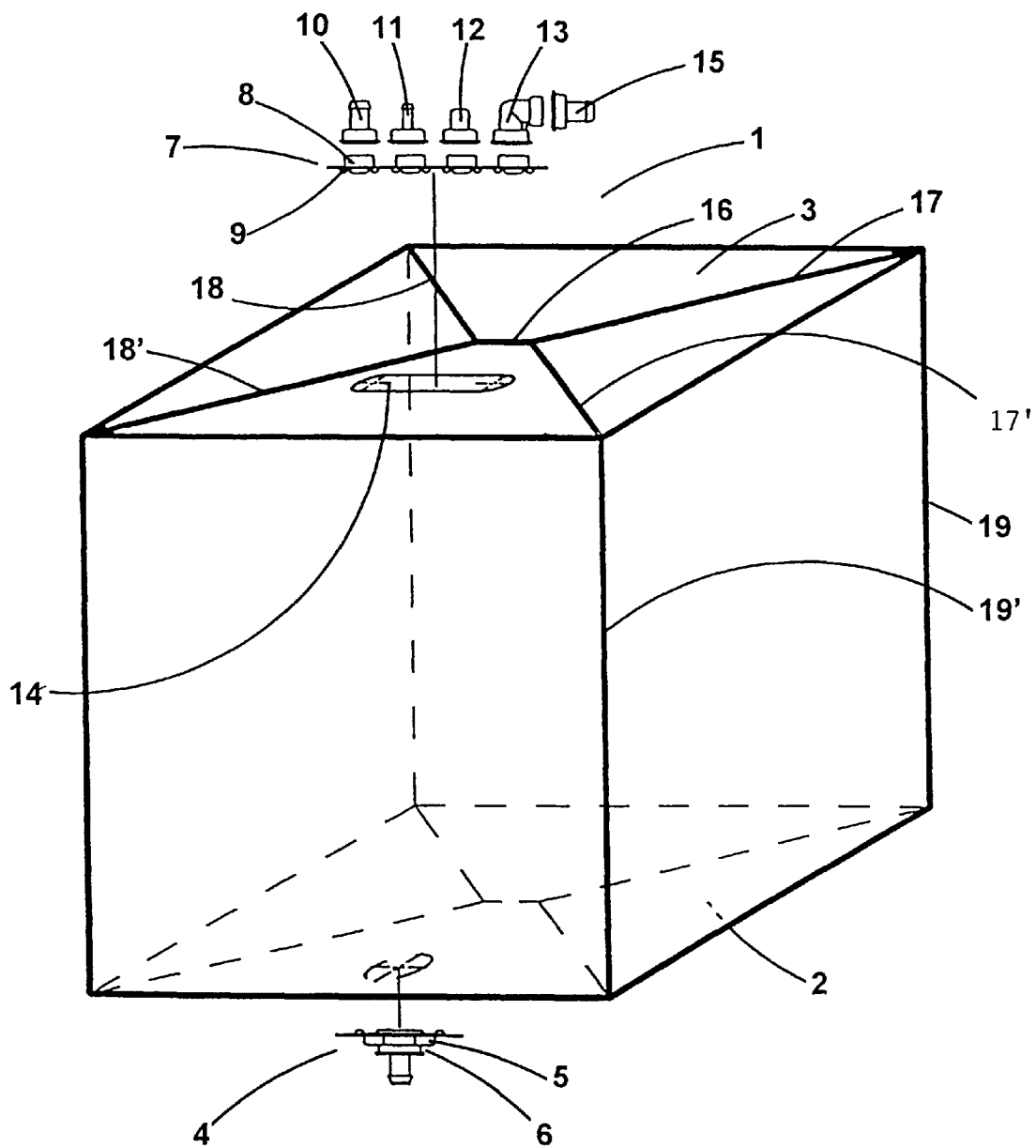
FIG. 1 is a perspective view of a sachet in accordance with the invention in the configuration that it assumes when filled, before fitting a bung and a connector mounting flange.

FIG. 1 shows a flexible sachet 1 in accordance with the invention comprising a bottom wall 2, a top wall 3 and four side walls. The bottom wall 2 is fitted with a bung 4 for draining off the bio-pharmaceutical liquid that it contains. The bung has an upstanding base 5, here of hexagonal shape, which can cooperate with an orifice of complementary shape in the bottom of a rigid container for transporting sachets. The base has a groove 6 for fitting a clip to immobilize the bung relative to the container, sandwiched between the bung base mounting flange and the clip.

A flange 7 for fitting connectors is fitted to the top face 3 of the container 1 (here it is shown separately from the sachet). The flange has four identical chimneys 8 each formed by two concentric lips. The end of each chimney inside the sachet includes four spaced semi-toroidal protuberances 9 with a gap between two successive protuberances 9. Connectors 10, 11, 12, 13 can be installed on these chimneys and here they are respectively connectors for large diameter tubes, for small diameter tubes, a stopper and a 90° elbow itself incorporating a chimney of similar construction to the previous ones and to which another connector 15 can be fitted, here of similar structure to the connector 10 for large diameter tubes.

This figure also shows the structure of the welds on the top and bottom face, firstly a weld 16 transverse to the advance movement of the films during fabrication of the sachet and welds inclined to this axis, welds 17 and 17' on the one hand (effected simultaneously) and welds 18 and 18' (also effected simultaneously). The lateral welds 19 and 19' are also effected simultaneously and likewise the welds parallel to them on the opposite face.

Finally, note an orifice 14 on the top wall 3 of the sachet for mounting the flange 7. The bottom wall 2 of the sachet also has an orifice for fitting the bung 4.

Figure 2:
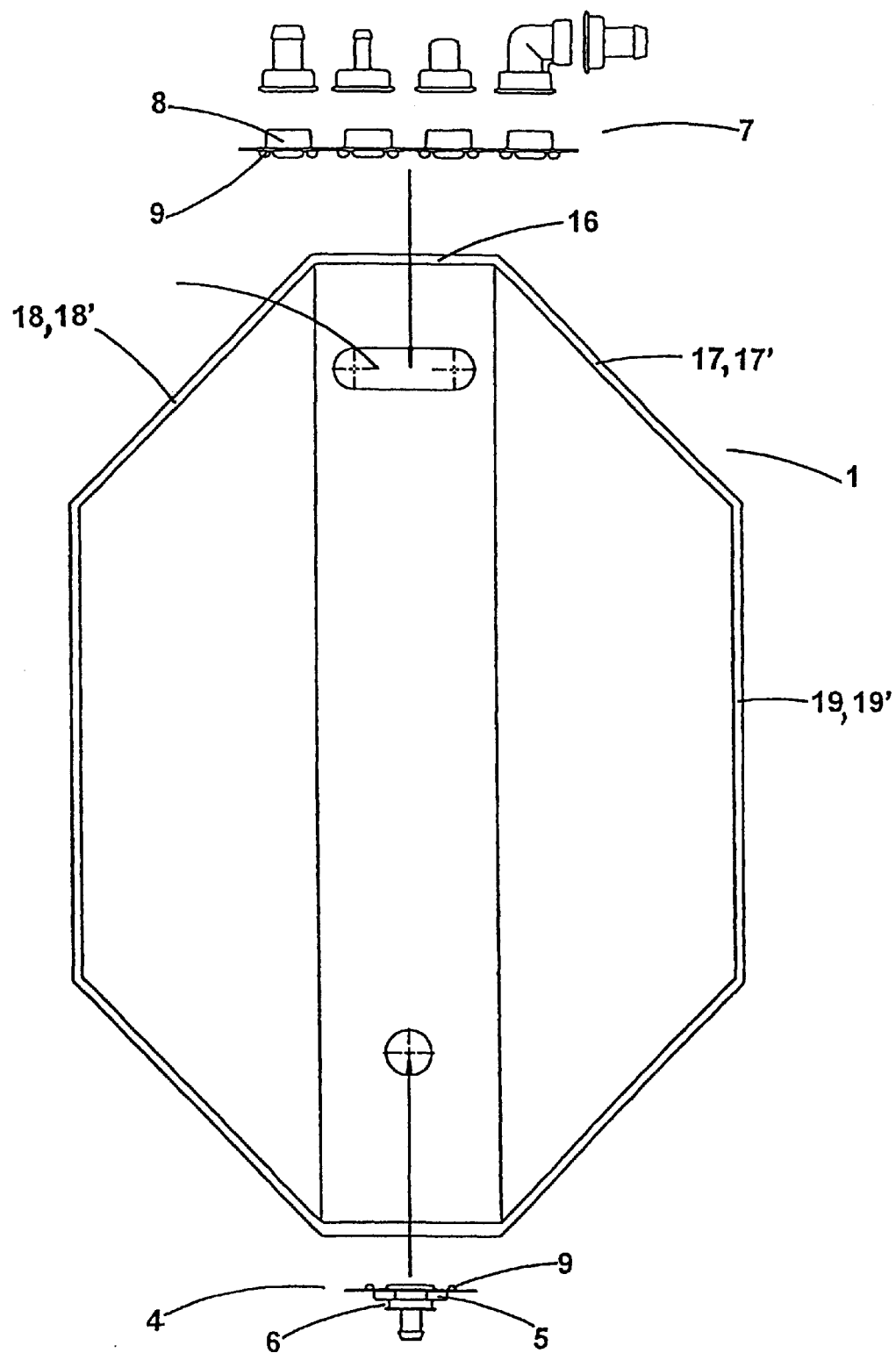
FIG. 2 represents a top view of a sachet when flat before fitting a bung and a connector mounting flange.

FIG. 2 shows the same components as FIG. 1 except that the sachet is flat, as immediately after fabrication. Accordingly the welds 17 and 17' can be seen to be superposed and likewise the welds 18, 18' and 19, 19'.

In this figure the flange 7 and the bung 4 are shown enlarged relative to the sachet 1. As further explained below, it can also be understood that in the central part of the sachet, where the orifices for the flange and the connector can be seen, there are only two thicknesses of laminated film, whereas at the sides there are four thicknesses of film.

FIG. 3, which illustrates the manufacture of a sachet in accordance with the invention, shows how the single laminated films are paid out. Two films 20 and 21 are tensioned flat, one at the top and one at the bottom, and two films 22 and 23 are conformed into flat bellows and inserted folded between the first two films. Two heating bars 24 and 25 sandwich the four thicknesses of film from the three different films 20, 21, 23 to produce two welds simultaneously. Similarly on the opposite side (the heating bars on the opposite side are not shown).

FIG. 4 shows the bars 26 and 27 which make the transverse welds at the top and bottom of the sachet (shown at 16 in FIGS. 1 and 2).

As mentioned above, it can be seen that using this manufacturing technique there are two areas 28 and 29 in which there are four thicknesses of film constituting the sachet whereas in an intermediate area 30 there are only two thicknesses. Nevertheless, given the particular structure of the films in accordance with the invention, flat fabrication produces welds and sachets of great strength, even during transportation over long distances.

FIG. 5 shows the principle of the "K" weld comprising, on the one hand, a weld perpendicular to the advance movement of the films, as shown in FIG. 4, and producing the weld 16, and two inclined welds 31 and 32 corresponding to those shown at 17, 17' and 18, 18' in FIGS. 1 and 2.

When the welding operations have been completed, the external parts of the films can obviously be cut off beyond the welded areas.

What is claimed is:

1. A method of manufacturing a flexible expandable sachet for transporting bio-pharmaceutical liquids with a volume of 50 liters or more and having a bellows construction which, when filled, takes on a substantially parallelepiped shape, the sachet comprising a bottom wall, a top wall and four lateral walls made of a single laminated film having at least three layers, an innermost layer of said layers being formed of plastic which is heat weldable and biocompatible with the bio-pharmaceutical liquid intended to be transported therein and at least one of (1) a flange on its top face for mounting connectors comprising at least one chimney comprising two substantially cylindrical concentric lips, and (2) a drain bung mounted on an outwardly upstanding base on the bottom of said sachet with an upstanding part of said bung having a non-circular shape, said method comprising:

making a top film, a bottom film and two lateral films, bolding said lateral films over themselves from said single laminated film, the innermost layer of said two folded over lateral films being on an exterior thereof with each folded over film having a folded edge;

stacking said top film, said bottom film and said two folded over lateral films with said two folded over lateral films located between said top film and said bottom film to bring surfaces of the stacked films into contact with each other with the folded edges of the two folded over lateral films facing one another with a gap therebetween;

heat welding outside edges of the stacked films to produce at least two side edges of the four lateral walls at a time; and further heat welding the stacked films to produce the bottom wall and the top wall.

2. The method claimed in claim 1, wherein top and bottom sachet welds are K welds and branches of the K welds are inclined at an angle in the range of 30° to 60° relative to a longitudinal axis of the stacked films.

3. The method claimed in claim 2, wherein one or two or three successive welds are effected at the position of a given weld.

4. The method claimed in claim 1, wherein said side edges are parallel.

5. The method claimed in claim 1, wherein welds produced by said heat welding have a width in a range of between 5 mm to 20 mm.

6. The method claimed in claim 1, wherein welds produced by said heat welding have a preferable width between a range of 5 mm to 15 mm.

7. The method claimed in claim 1, wherein welds produced by said heat welding have a particular width between 8 mm to 15 mm.

8. A method of manufacturing a flexible expandable sachet for transporting bio-pharmaceutical liquids which, when filled, takes on a substantially parallelepiped shape, the sachet comprising a bottom wall, a top wall and four lateral walls made of a single laminated film having at least three layers, an innermost layer of said layers being formed of plastic which is heat weldable and biocompatible with the bio-pharmaceutical liquid intended to be transported therein, said method comprising:

making a top film, a bottom film and two lateral films, said lateral films being folded over from said single laminated film, the innermost layer of said two folded over lateral films being on an exterior thereof with each folded over film having a folded edge;

stacking said top film, said bottom film and said two folded over lateral films with said two folded over lateral films located between said top film and said bottom film to bring surfaces of the stacked films into contact with each other with the folded edges of the two folded over lateral films facing one another with a gap therebetween;

heat welding outside edges of the stacked films to produce at least two side edges of the four lateral walls at a time; and further heat welding the stacked films to produce the bottom wall and the top wall;

wherein top and bottom sachet welds are K welds and branches of the K welds are inclined at an angle in the range of 30° to 60° relative to a longitudinal axis of the stacked films;

wherein one or two or three successive welds are effected at the position of a given weld;

wherein said successive welds are made at different temperatures.

9. A method of manufacturing a flexible expandable sachet for transporting bio-pharmaceutical liquids which, when filled, takes on a substantially parallelepiped shape, the sachet comprising a bottom wall, a top wall and four lateral walls made of a single laminated film having at least three layers, an innermost layer of said layers being formed of plastic which is heat weldable and biocompatible with the bio-pharmaceutical liquid intended to be transported therein, said method comprising:

making a top film, a bottom film and two lateral films, said lateral films being folded over from said single laminated film, the innermost layer of said two folded over lateral films being on an exterior thereof with each folded over film having a folded edge;

stacking said top film, said bottom film and said two folded over lateral films with said two folded over lateral films located between said top film and said bottom film to bring surfaces of the stacked films into contact with each other with the folded edges of the two folded over lateral films facing one another with a gap therebetween;

heat welding outside edges of the stacked films to produce at least two side edges of the four lateral walls at a time; and further heat welding the stacked films to produce the bottom wall and the top wall;

wherein an external layer of said single laminated film has an insulating effect to heat welding.

\* \* \* \* \*